(12) United States Patent
Parikh et al.

(10) Patent No.: US 6,558,952 B1
(45) Date of Patent: May 6, 2003

(54) TREATMENT FOR DIABETES

(75) Inventors: Indu Parikh, Chapel Hill, NC (US); Anne Lane, Westmount (CA); Ronald V. Nardi, Mahwah, NJ (US); Stephen J. Brand, Lincoln, MA (US)

(73) Assignees: Waratah Pharmaceuticals, Inc., Quebec (CA); The General Hospital Corporation, Boston, MA (US)

( * ) Notice: Subject to any disclaimer, the term of this patent is extended or adjusted under 35 U.S.C. 154(b) by 0 days.

(21) Appl. No.: 09/241,100

(22) Filed: Jan. 29, 1999

Related U.S. Application Data

(63) Continuation-in-part of application No. 09/127,028, filed on Jul. 30, 1998, now Pat. No. 6,288,301, which is a continuation of application No. 07/992,255, filed on Dec. 14, 1992, now Pat. No. 5,885,956.

(51) Int. Cl.$^7$ .............................. C12N 5/00; C12N 5/02; C12N 5/08; C07K 7/00; A61K 35/00

(52) U.S. Cl. ...................... 435/384; 435/383; 435/366; 435/325; 435/320.1; 530/309; 530/399; 514/2; 514/44; 514/309; 514/399; 514/866; 424/93.1

(58) Field of Search ............................. 514/2, 44, 866, 514/399, 309; 424/93.1; 435/320.1, 325, 366, 383, 384; 530/309, 399

(56) References Cited

U.S. PATENT DOCUMENTS 5,587,309 A * 12/1996 Rubin et al. .............. 435/240.2
5,885,956 A *  3/1999 Nardi et al. .................... 514/2

FOREIGN PATENT DOCUMENTS

WO    WO 95/19785    5/1995

OTHER PUBLICATIONS

Rooth et al. Diabetes. 38, Suppl. 1: 202–5, Jan. 1989.*
Beger et al. Transplantation. 63(4): 577–82, Feb. 1997.*
Efrat, S. Diabetologia. 41: 1401–9, Dec. 1998.*
Wennberg et al. Transplantation. 63(9): 1234–42, May 1997.*
Korc et al. Journal of Clinical Investigation. 92: 1113–4, Sep. 1993.*
Playford et al. Gastroenterology. 108(1): 92–101, Jan. 1995.*
Goodlad et al. Clin. Sci. (Colch). 91(4): 503–7, Oct. 1996.*
Brand et al. J. Biol. Chem. 263(11): 5341–7, Apr. 1988.*
Sandgren et al. Cell. 61:1121–1135, Jun. 1990.*
Jhappan et al. Cell. 61: 1137–1146, Jun. 1990.*
Wang, et al. *J. Clin. Invest.* (1993), 92:1349–56.
Baldwin and Zhang (1992) *Cancer Research* 52: 2261–2267.
Benhamou et al. (1998 Jun.) *Diabetes Metab.* 24(3):215–224.
Berube, F.L. et al. (1993) *J. Pediatr. Gastroenterol. Nutr.* 17: 39–48.
Boshart et al (1985) *Cell* 41:521–530.
Bouwens and Pipeleers (1998) *Diabetologia* 41:629.
Brand and Fuller (1988) *J. Biol. Chem.* 263:5341.
Carpenter and Wahl in Peptide Growth Factors (Sporn & Roberts, eds.), Springer–Verlag, 1990.
Christiansen et al. (1994 Dec.) *J. Clin. Endocrinol. Metab.* 79(6):1561–1569.
Fraga et al. (1998 Apr.) *Transplantation* 65(8): 1060–1066.
Heitz et al (1977) *Diabetes* 26:632–642.
Hollande et al (1976) *Gastroenterology* 71:251–262.
Kantaman and Sharp (1982) *Mol. Cell Biol.* 2:1304–1319.
Kappel et al. (1993) *Current Opinion in Biotechnology* 3: 548–553.
Kendall et al. (1996 Jun.) *Diabetes Metab.* 22(3):157.
Korsgren et al. (1993) *Ups. J. Med. Sci.* 98(1):39–52.
Newgard et al. (1997 Jul.) *Diabetologiz 40 Suppl.* 2:S42–S47.
Ryberg et al. (1990) *Gastroenterology* 98:33–38.
Sandler et al. (1997 Jun.) *Transplantation* 63(12):1712.
Sasaki et al. (Jun. 15, 1998) *Transplantation* 65(11):1510.
Soon–Shiong et al. (1990 Jun.) *Postgrad. Med.* 87(8):133.
Soon–Shiong et al. (1992 Nov.) *Transplantation* 54(5):769–774.
Soon–Shiong et al. (1992 Oct.) *ASAIO J.* 38(4):851–854.
Soon–Shiong et al. (1993 Jun.) *Proc. Natl. Acad. Sci. USA* 90(12):5843–5847.
Soon–Shiong et al. (1994) *Lancet* 343:950–951.
Subramani et al. (1981) *Mol. Cell Bio* 1:854–864.
Suzuki et al. (1998 Jan.) *Cell Transplant* 7(1):47–52.
Teitelman et al (1987) *Develop. Biology* 121: 454–466.
Vinter–Jensen, L. et al. (1997) *Gastroenterology* 113:1367–1374.
Wang et al. (1997) *Diabetologia* 40: 886–893.
Watanabe, T. et al. (1994) *Proc. Natl. Acad. Sci. USA* 91:3589–3592.
Zhou et al. (1998 May) *Am. J. Physiol.* 274(5 Pt 1):C1356.

* cited by examiner

*Primary Examiner*—Anne M. Wehbe'
(74) *Attorney, Agent, or Firm*—Barbara Rae-Venter; Rae-Venter Law Group

(57) ABSTRACT

Methods and compositions for treating diabetes mellitus in a patient in need thereof are provided. The methods include administering to a patient a composition providing a gastrin/CCK receptor ligand, e.g., a gastrin, and/or an epidermal growth factor (EGF) receptor ligand, e.g., TGF-α, in an amount sufficient to effect differentiation of pancreatic islet precursor cells to mature insulin-secreting cells. The composition can be administered systemically or expressed in situ by cells transgenically supplemented with one or both of a gastrin/CCK receptor ligand gene, e.g., a preprogastrin peptide precursor gene and an EGF receptor ligand gene, e.g., a TGF-α gene. The methods also include transplanting into a patient cultured pancreatic islets in which mature insulin-secreting beta cells are proliferated by exposure to a gastrin/CCK receptor ligand and an EGF receptor ligand.

3 Claims, 8 Drawing Sheets

(1 of 8 Drawing Sheet(s) Filed in Color)

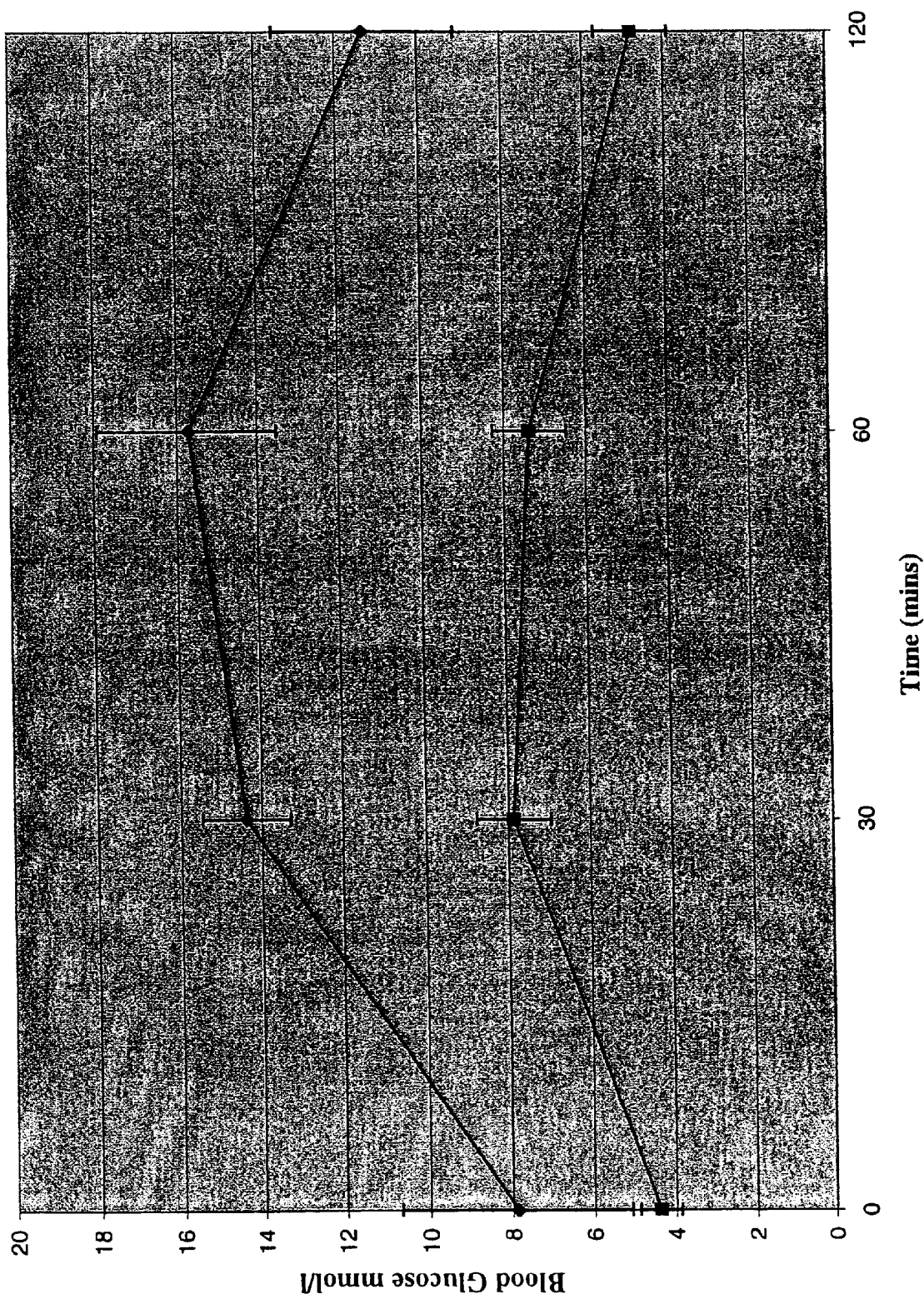

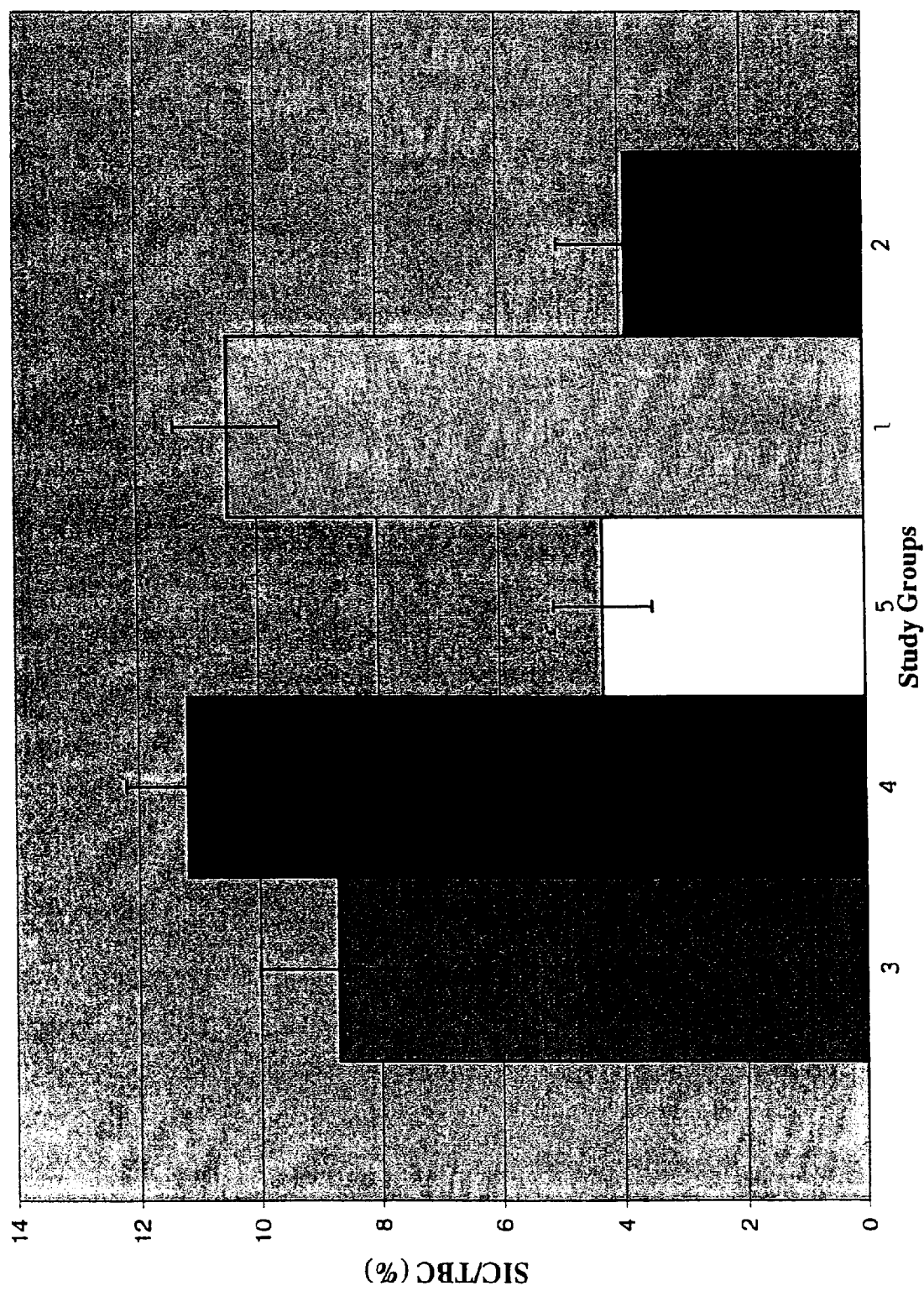

TREATMENT FOR DIABETES

CROSS-REFERENCE TO RELATED APPLICATIONS

This application is a continuation-in-part of U.S. Ser. No. 09/127,028, filed Jul. 30, 1998, now U.S. Pat. No. 6,288,301, which is a continuation U.S. Ser. No. of 07/992,255, filed Dec. 14, 1992, which issued Mar. 23, 1999, as U.S. Pat. No. 5,885,956, which disclosures are incorporated herein by reference.

GOVERNMENT LICENSE RIGHTS

This invention was made with U.S. Government support under Contract 5 R01 DK 42147-04 awarded by the National Institutes of Health. The U.S. Government has certain rights in this invention.

INTRODUCTION

1. Field of the Invention

This invention relates to a method for treating diabetes mellitus in an individual in need thereof by administering to the individual a composition comprising a gastrin/CCK receptor ligand and/or an EGF receptor ligand which effectively promotes differentiation of pancreatic islet precursor cells to mature insulin-secreting cells. The method is exemplified by administration of gastrin and transforming growth factor alpha (TGF-$\alpha$) either alone or in combination to normal streptozotocin (STZ) induced diabetic and genetically predisposed diabetic Zucker rats.

2. Background

Diabetes is one of the most common endocrine diseases across all age groups and populations. In addition to the clinical morbidity and mortality, the economic cost of diabetes is huge, exceeding $90 billion per year in the US alone, and the prevalence of diabetes is expected to increase more than two-fold by the year 2010.

There are two major forms of diabetes mellitus: insulin-dependent (Type 1) diabetes mellitus (IDDM) which accounts for 5 to 10% of all cases, and non-insulin-dependent (Type 2) diabetes mellitus (NIDDM) which comprises roughly 90% of cases. Type 2 diabetes is associated with increasing age however there is a trend of increasing numbers of young people diagnosed with NIDDM, so-called maturity onset diabetes of the young (MODY). In both Type 1 and Type 2 cases, there is a loss of insulin secretion, either through destruction of the $\beta$-cells in the pancreas or defective secretion or production of insulin. In NIDDM, patients typically begin therapy by following a regimen of an optimal diet, weight reduction and exercise. Drug therapy is initiated when these measures no longer provide adequate metabolic control. Initial drug therapy includes sulfonylureas that stimulate $\beta$-cell insulin secretion, but also can include biguanides, $\alpha$-glucosidase inhibitors, thiazolidenediones and combination therapy. It is noteworthy however that the progressive nature of the disease mechanisms operating in type 2 diabetes are difficult to control. Over 50% of all drug-treated diabetics demonstrate poor glycemic control within six years, irrespective of the drug administered. Insulin therapy is regarded by many as the last resort in the treatment of Type 2 diabetes, and there is patient resistance to the use of insulin.

Pancreatic islets develop from endodermal stem cells that lie in the fetal ductular pancreatic endothelium, which also contains pluripotent stem cells that develop into the exocrine pancreas. Teitelman and Lee, *Developmental Biology*, 121:454–466 (1987); Pictet and Rutter, *Development of the embryonic encocrine pancreas, in Endocrinology, Handbook of Physiology*, ed. R. O. Greep and E. B. Astwood (1972), American Physiological Society: Washington, D.C., p.25–66. Islet development proceeds through discrete developmental stages during fetal gestation which are punctuated by dramatic transitions. The initial period is a protodifferentiated state which is characterized by the commitment of the pluripotent stem cells to the islet cell lineage, as manifested by the expression of insulin and glucagon by the protodifferentiated cells. These protodifferentiated cells comprise a population of committed islet precursor cells which express only low levels of islet specific gene products and lack the cytodifferentiation of mature islet cells. Pictet and Rutter, supra. Around day 16 in mouse gestation, the protodifferentiated pancreas begins a phase of rapid growth and differentiation characterized by cytodifferentiation of islet cells and a several hundred fold increase in islet specific gene expression. Histologically, islet formation (neogenesis) becomes apparent as proliferating islets bud from the pancreatic ducts (nesidioblastosis). Just before birth the rate of islet growth slows, and islet neogenesis and nesidioblastosis becomes much less apparent. Concomitant with this, the islets attain a fully differentiated state with maximal levels of insulin gene expression. Therefore, similar to many organs, the completion of cellular differentiation is associated with reduced regenerative potential; the differentiated adult pancreas does not have either the same regenerative potential or proliferative capacity as the developing pancreas.

Since differentiation of protodifferentiated precursors occurs during late fetal development of the pancreas, the factors regulating islet differentiation are likely to be expressed in the pancreas during this period. One of the genes expressed during islet development encodes the gastrointestinal peptide, gastrin. Although gastrin acts in the adult as a gastric hormone regulating acid secretion, the major site of gastrin expression in the fetus is the pancreatic islets. Brand and Fuller, *J. Biol Chem.*, 263:5341–5347 (1988). Expression of gastrin in the pancreatic islets is transient. It is confined to the period when protodifferentiated islet precursors form differentiated islets. Although the significance of pancreatic gastrin in islet development is unknown, some clinical observations suggest a rule for gastrin in this islet development as follows. For example, hypergastrinemia caused by gastrin-expressing islet cell tumors and atrophic gastritis is associated with nesidioblastosis similar to that seen in differentiating fetal islets. Sacchi, et al., *Virchows Archiv* B, 48:261–276 (1985); and Heitz et al., *Diabetes*, 26:632–642 (1977). Further, an abnormal persistence of pancreatic gastrin has been documented in a case of infantile nesidioblastosis. Hollande, et al., *Gastroenterology*, 71:251–262 (1976). However, in neither observation was a causal relationship established between the nesidioblastosis and gastrin stimulation.

It is therefore of interest to identify agents that stimulate islet cell regeneration which could be of value in the treatment of early IDDM and in the prevention of $\beta$-cell deficiency in NIDDM.

Citations of a reference herein shall not be construed as an admission that such reference is prior art to the present invention.

RELEVANT LITERATURE

Three growth factors are implicated in the development of the fetal pancreas, gastrin, transforming growth factor $\alpha$ (TGF-α) and epidermal growth factor (EGF) (Brand and Fuller, *J. Biol. Chem.* 263:5341–5347). Transgenic mice over expressing TGF-α or gastrin alone did not demonstrate active islet cell growth, however mice expressing both transgenes displayed significantly increased islet cell mass (Wang et al, (1993) *J Clin Invest* 92:1349–1356). Bouwens and Pipeleers (1998) *Diabetoligia* 41:629–633 report that there is a high proportion of budding β-cells in the normal adult human pancreas and 15% of all , β-cells were found as single units. Single β-cell foci are not commonly seen in adult (unstimulated) rat pancreas; Wang et al ((1995) *Diabetologia* 38:1405 –1411) report a frequency of approximately 1% of total β-cell number.

Insulin independence in a Type 1 diabetic patient after encapsulated islet transplantation is described in Soon-Shiong et al (1994) *Lancet* 343:950–51. Also see Sasaki et al (Jun. 15, 1998)*Transplantation* 65(11):1510–1512; Zhou et al (May 1998) *Am J Physiol* 274(5 Pt 1):C1356–1362; Soon-Shiong et al (June 1990)*Postgrad Med* 87(8): 133–134; Kendall et al (June 1996) *Diabetes Metab* 22(3): 157–163; Sandler et al (June 1997) *Transplantation* 63(12): 1712–1718; Suzuki et al (January 1998) *Cell Transplant* 7(1):47–52; Soon-Shiong et al (June 1993) *Proc Natl Acad Sci* USA 90(12):5843–5847; Soon-Shiong et al (November 1992) *Transplantation* 54(5):769–774; Soon-Shiong et al (October 1992) *ASAIO J* 38(4):851–854; Benhamou et al (June 1998 ) *Diabetes Metab* 24(3):215–224; Christiansen et al (December 1994) *J Clin Endocrinol Metab* 79(6): 1561–1569; Fraga et al (April 1998) *Transplantation* 65(8): 1060–1066; Korsgren et al (1993) *Ups J Med Sci* 98(1): 39–52; Newgard et al (July 1997) *Diabetologiz* 40 *Suppl* 2:S42–S47.

SUMMARY OF THE INVENTION

The invention provides methods for treating diabetes mellitus in a patient in need thereof by administering a composition providing a gastrin/CCK receptor ligand, an EGF receptor ligand, or a combination of both in an amount sufficient to effect differentiation of the patient's pancreatic islet precursor cells to mature insulin-secreting cells. The composition can be administered systemically or expressed in situ by host cells containing a nucleic acid construct in an expression vector wherein the nucleic acid construct comprises a coding sequence for a gastrin CCK receptor ligand or a coding sequence for an EGF receptor ligand, together with transcriptional and translational regulatory regions functional in pancreatic islet precursor cells. Also provided are methods and compositions for treating diabetes in a patient in need thereof by implanting into a diabetic patient pancreatic islet cells that have been grown in culture by exposure to a sufficient amount of a gastrin/CCK receptor ligand and/or an EGF receptor ligand to increase the number of pancreatic beta cells in the islets from pancreatic islet precursor cells; optionally the population of pancreatic beta cells or pancreatic islet precursor cells can be grown in culture for a time sufficient to expand the population of β-cells prior to transplantation. The methods and compositions find use in treating patients with diabetes.

The file of this patent contains at least one drawing executed in color. Copies of this patent with color drawing (s) will be provided by the Patent and Trademark Office upon request and payment of the necessary fee.

BRIEF DESCRIPTION OF THE DRAWINGS

The file of this patent contains at least one drawing executed in color. Copies of this patent with color drawings are provided to the Patent and Trademark Office with payment of the necessary fee.

FIG. 5 shows the effects of TGF-α and gastrin on glucose tolerance in streptozotocin induced diabetic Wistar rats treated with PBS (open circles) or a combination of TGF-α and gastrin i.p. daily for 10 days (open squares).

FIG. 6 shows the effect of TGF-α and gastrin treatment on β-cell neogenesis in three groups of treated Zucker rats together with the corresponding PBS controls (n=6 per group) as described in Example 7. The bar corresponding to group 1 represents lean TFG+gastrin, the bar corresponding to group 4 represents ob TGF+gastrin, the bar corresponding to group 5 represents the ob PBS control, the bar corresponding to group 3 represents pre TFG+gastrin and the bar corresponding to group 2 represents the lean PBS control. TGF-α and gastrin significantly increased the relative proportion of single β-cell foci in all the groups studied as compared to PBS-treated control animals. Groups 4 and 5 are significantly different (p<0.0015) as are Groups 1 and 2 (p<0.0041).

DETAILED DESCRIPTION OF PREFERRED EMBODIMENTS

Figure 1A:
FIG. 1A is an image that shows numerous insulin staining cells in the metaplastic ducts from the TGF-α transgenic pancreas upon immunoperoxidase staining.

The invention provides methods for treating diabetes mellitus in a patient in need thereof by administering a composition providing a gastrin/CCK receptor ligand such as gastrin, an EGF receptor ligand, such as TGF-α, or a combination of both in an amount sufficient to effect differentiation of pancreatic islet precursor cells to mature insulin-secreting cells. When the composition is administered systemically, generally it is provided by injection, preferably intravenously, in a physiologically acceptable carrier. When the composition is expressed in situ, pancreatic islet precursor cells are transformed either in ex vivo or in vivo with one or more nucleic acid expression constructs in an expression vector which provides for expression of the desired receptor ligand(s) in the pancreatic islet precursor cells. As an example, the expression construct includes a coding sequence for a CCK receptor ligand, such as preprogastrin peptide precursor coding sequence which, following expression, is processed to gastrin or a coding sequence for an EGF receptor ligand such as TGF-α, together with transcriptional and translational regulatory regions which provide for expression in the pancreatic islet precursor cells. The transcriptional regulatory region can be constitutive or induced, for example by increasing intracellular glucose concentrations, such as a transcriptional regulatory region from an insulin gene. Transformation is carried out using any suitable expression vector, for example, an adenoviral expression vector. When the transformation is carried out ex vivo, the transformed cells or tissues are implanted in the diabetic patient, for example using a kidney capsule. Alternatively, pancreatic islet tissue containing islet precursor cells are treated ex vivo with a sufficient amount of a gastrin/CCK receptor ligand and/or an EGF receptor ligand to increase the number of pancreatic β cells in the islets prior to implantation into the diabetic patient. As required, the population of insulin-secreting pancreatic β cells is expanded in culture prior to implantation by contacting pancreatic islet precursor cells with the same receptor ligand (s).

The subject invention offers advantages over existing treatment regimens for diabetic patients. By providing a means to stimulate the adult pancreas to regenerate, not only is the need for traditional drug therapy (Type 2) or insulin therapy (Type 1 and Type 2) reduced or even eliminated, but the maintenance of normal blood glucose levels also may reduce some of the more debilitating complications of diabetes. Diabetic complications include those affecting the small blood vessels in the retina, kidney, and nerves, (microvascular complications), and those affecting the large blood vessels supplying the heart, brain, and lower limbs (mascrovascular complications). Diabetic microvascular complications are the leading cause of new blindness in people 20–74 years old, and account for 35% of all new cases of end-stage renal disease. Over 60% of diabetics are affected by neuropathy. Diabetes accounts for 50% of all non-traumatic amputations in the USA, primarily as a result of diabetic macrovascular disease, and diabetics have a death rate from coronary artery disease that is 2.5 times that of non-diabetics. Hyperglycemia is believed to initiate and accelerate progression of diabetic microvascular complications. Use of the various current treatment regimens cannot adequately control hyperglycemia and therefore does not prevent or decrease progression of diabetic complications.

As used herein, the term "gastrin/CCK receptor ligand" encompasses compounds that stimulate the gastrin/CCK receptor. Examples of such gastrin/CCK receptor ligands include various forms of gastrin such as gastrin 34 (big gastrin), gastrin 17 (little gastrin), and gastrin 8 (mini gastrin); various forms of cholecystokinin such as CCK 58, CCK 33, CCK 22, CCK 12 and CCK 8; and other gastrin/CCK receptor ligands that either alone or in combination with EGF receptor ligands can induce differentiation of cells in mature pancreas to form insulin-secreting islet cells. Also contemplated are active analogs, fragments and other modifications of the above. Such ligands also include compounds that increase the secretion of endogenous gastrins, cholecystokinins or similarly active peptides from sites of tissue storage. Examples of these are omeprazole which inhibits gastric acid secretion and soy bean trypsin inhibitor which increases CCK stimulation.

As used herein, the term "EGF receptor ligand" encompasses compounds that stimulate the EGF receptor such that when gastrin/CCK receptors in the same or adjacent tissues or in the same individual also are stimulated, neogenesis of insulin-producing pancreatic islet cells is induced. Examples of such EGF receptor ligands include EGF1–53, and fragments and active analogs thereof, including EGF1–48, EGF1–52, EGF1–49. See, for example, U.S. Pat. No. 5,434,135. Other examples include TGF-α receptor ligands (1–50) and fragments and active analogs thereof, including 1–48, 1–47 and other EGF receptor ligands such as amphiregulin and pox virus growth factor as well as other EGF receptor ligands that demonstrate the same synergistic activity with gastrin/CCK receptor ligands. These include active analogs, fragments and modifications of the above. For further background, see Carpenter and Wahl, Chapter 4 in *Peptide Growth Factors* (Eds. Sporn and Roberts), Springer Verlag, (1990).

A principal aspect of the invention is a method for treating diabetes mellitus in an individual in need thereof by administering to the individual a composition including a gastrin/CCK receptor ligand and/or an EGF receptor ligand in an amount sufficient to effect differentiation of pancreatic islet precursor cells to mature insulin-secreting cells. The cells so differentiated are residual latent islet precursor cells in the pancreatic duct. One embodiment comprises administering, preferably systemically, a differentiation regenerative amount of a gastrin/CCK receptor ligand and an EGF receptor ligand, preferably TGF-α, either alone or in combination to the individual.

Another embodiment comprises providing a gastrin/CCK receptor ligand and/or an EGF receptor ligand to pancreatic islet precursor cells of explanted pancreatic tissue of a mammal and reintroducing the pancreatic tissue so stimulated to the mammal.

In another, the invention comprises providing a gastrin/CCK receptor ligand and/or an EGF receptor ligand to pancreatic islet precursor cells of explanted pancreatic tissue from a mammal to expand the population of β cells.

In another embodiment gastrin/CCK receptor ligand stimulation is effected by expression of a chimeric insulin promoter-gastrin fusion gene construct transgenically introduced into such precursor cells. In another embodiment EGF receptor ligand stimulation is effected by expression of an EGF receptor ligand gene transgenically introduced into the mammal. The sequence of the EGF gene is provided in U.S. Pat. No. 5,434,135.

In another embodiment stimulation by a gastrin/CCK receptor ligand and an EGF receptor ligand is effected by coexpression of (i) a preprogastrin peptide precursor gene and (ii) an EGF receptor ligand gene that have been stably introduced into the mammal.

In another aspect the invention relates to a method for effecting the differentiation of pancreatic islet precursor cells of a mammal by stimulating such cells with a combination of a gastrin/CCK receptor ligand and an EGF receptor ligand. In a preferred embodiment of this aspect, gastrin stimulation is effected by expression of a preprogastrin peptide precursor gene stably introduced into the mammal. The expression is under the control of the insulin promoter. EGF receptor ligand, e.g., TGF-α, stimulation is effected by expression of an EGF receptor ligand gene transgenically introduced into the mammal. In furtherance of the above, stimulation by a gastrin and a TGF-α is preferably effected by co-expression of (i) a preprogastrin peptide precursor gene and (ii) an EGF receptor ligand introduced into the mammal. Appropriate promoters capable of directing transcription of the genes include both viral promoters and cellular promoters. Viral promoters include the immediate early cytomegalovirus (CMV) promoter (Boshart et al (1985) *Cell* 41:521–530), the SV40 promoter (Subramani et al (1981) *Mol. Cell. Biol.* 1–854–864) and the major late promoter from Adenovirus 2 (Kaufman and Sharp (1982) *Mol. Cell. Biol.* 2:1304–13199). Preferably, expression of one or both of the gastrin/CCK receptor ligand gene and the EGF receptor ligand gene is under the control of an insulin promoter.

Another aspect of the invention is a nucleic acid construct. This construct includes a nucleic acid sequence coding for a preprogastrin peptide precursor and an insulin transcriptional regulatory sequence, which is 5' to and effective to support transcription of a sequence encoding the preprogastrin peptide precursor. Preferably, the insulin transcriptional regulatory sequence includes at least an insulin promoter. In a preferred embodiment the nucleic acid sequence coding for the preprogastrin peptide precursor comprises a polynucleotide sequence containing exons 2 and 3 of a human gastrin gene and optionally also including introns 1 and 2.

Another embodiment of the invention is an expression cassette comprising (i) a nucleic acid sequence coding for a mammalian EGF receptor ligand, e.g., TGF-α and a transcriptional regulatory sequence thereof; and (ii) a nucleic acid sequence coding for the preprogastrin peptide precursor and a transcriptional regulatory sequence thereof. Preferably, the transcriptional regulatory sequence for the EGF receptor ligand is a strong non-tissue specific promoter, such as a metallothionein promoter. Preferably, the transcriptional regulatory sequence for the preprogastrin peptide precursor is an insulin promoter. A preferred form of this embodiment is one wherein the nucleic acid sequence coding for the preprogastrin peptide precursor comprises a polynucleotide sequence containing introns 1 and 2 and exon 2 and 3 of the human gastrin gene.

Another aspect of the invention relates to a vector including the expression cassette comprising the preprogastrin peptide precursor coding sequence. This vector can be a plasmid such as pGem1 or can be a phage which has a transcriptional regulatory sequence including an insulin promoter.

Another aspect of this invention relates to a composition of vectors including (1) having the nucleic acid sequence coding for a mammalian EGF receptor ligand, e.g., TGF-α, under control of a strong non-tissue specific promoter, e.g., a metallothionein promoter; and a preprogastrin peptide precursor coding sequence under control of an insulin promoter. Each vector can be a plasmid, such as plasmid pGem1 or a phage in this aspect. Alternatively, the expression cassette or vector also can be inserted into a viral vector with the appropriate tissue trophism. Examples of viral vectors include adenovirus, *Herpes simplex* virus, adeno-associated virus, retrovirus, lentivirus, and the like. See Blomer et al (1996) *Human Molecular Genetics* 5 Spec. No: 1397–404; and Robbins et al (1998) *Trends in Biotechnology* 16:35–40. Adenovirus-mediated gene therapy has been used successfully to transiently correct the chloride transport defect in nasal epithelia of patients with cystic fibrosis. See Zabner et a. (1993) *Cell* 75:207–216.

Another aspect of the invention is a non-human mammal or mammalian tissue, including cells, thereof capable of expressing a stably integrated gene which encodes preprogastrin. Another embodiment of this aspect is a non-human mammal capable of coexpressing (i) a preprogastrin peptide precursor gene; and/or (ii) an EGF receptor ligand, e.g., a TGF-α gene that has been stably integrated into the non-human mammal, mammalian tissue or cells. The mammalian tissue or cells can be human tissue or cells.

Therapeutic Administration and Compositions

Modes of administration include but are not limited to transdermal, intramuscular, intraperitoneal, intravenous, subcutaneous, intranasal, and oral routes. The compounds can be administered by any convenient route, for example by infusion or bolus injection by absorption through epithelial or mucocutaneous linings (e.g., oral mucosa, rectal and intestinal mucosa, etc.) and can be administered together with other biologically active agents. Administration is preferably systemic.

The present invention also provides pharmaceutical compositions. Such compositions comprise a therapeutically effective amount of a therapeutic, and a pharmaceutically acceptable carrier or excipient. Such a carrier includes but is not limited to saline, buffered saline, dextrose, water, glycerol, ethanol, and combinations thereof. The formulation should suit the mode of administration. Pharmaceutically acceptable carriers and formulations for use in the present invention are found in Remington's *Pharmaceutical Sciences*, Mack Publishing Company, Philadelphia, Pa., 17$^{th}$ ed. (1985), which is incorporated herein by reference. For a brief review of methods for drug delivery, see Langer (1990) *Science* 249:1527–1533, which is incorporated herein by reference.

In preparing pharmaceutical compositions of the present invention, it may be desirable to modify the compositions of the present invention to alter their pharmacokinetics and biodistribution. For a general discussion of pharmacokinetics, see Remingtons's *Pharmaceutical Sciences*, supra, Chapters 37–39. A number of methods for altering pharmacokinetics and biodistribution are known to one of ordinary skill in the art (See, e.g., Langer, supra). Examples of such methods include protection of the agents in vesicles composed of substances such as proteins, lipids (for example, liposomes), carbohydrates, or synthetic polymers. For example, the agents of the present invention can be incorporated into liposomes in order to enhance their pharmacokinetics and biodistribution characteristics. A variety of methods are available for preparing liposomes, as described in, e.g., Szoka et al (1980) *Ann. Rev. Biophys. Bioeng.* 9:467, U.S. Pat. Nos. 4,235,871, 4,501,728 and 4,837,028, all of which are incorporated herein by reference. Various other delivery systems are known and can be used to administer a therapeutic of the invention, e.g., microparticles, microcapsules and the like.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures such as a pharmaceutical composition adapted for intravenous administration to human beings. Typically, compositions for intravenous administration are solutions in sterile isotonic aqueous buffer. Where necessary, the composition also can include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampoule or sachette indicating the quality of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium and other divalent cations, isopropylamine, triethylamine, 2-ethylamino ethanol, histidine, procaine, etc.

The amount of the therapeutic of the invention which is effective in the treatment of a particular disorder or condition will depend on the nature of the disorder or condition, and can be determined by standard clinical techniques. The precise dose to be employed in the formulation also will depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective dosages can be extrapolated from dose-response curves derived from in vitro or animal model test systems. Suppositories generally contain active ingredient in the range of 0.5% to 10% weight; oral formulations preferably contain 10% to 95% active ingredient.

In the gene therapy methods of the invention, transfection in vivo is obtained by introducing a therapeutic transcription or expression vector into the mammalian host, either as naked DNA, complexed to lipid carriers, particularly cationic lipid carriers, or inserted into a viral vector, for example a recombinant adenovirus. The introduction into the mammalian host can be by any of several routes, including intravenous or intraperitoneal injection, intratracheally, intrathecally, parenterally, intraarticularly, intranasally, intramuscularly, topically, transdermally, application to any mucous membrane surface, corneal installation, etc. Of particular interest is the introduction of the therapeutic expression vector into a circulating bodily fluid or into a body orifice or cavity. Thus, intravenous administration and intrathecal administration are of particular interest since the vector may be widely disseminated following such routes of administration, and aerosol administration finds use with introduction into a body orifice or cavity. Particular cells and tissues can be targeted, depending upon the route of administration and the site of administration. For example, a tissue which is closest to the site of injection in the direction of blood flow can be transfected in the absence of any specific targeting. If lipid carriers are used, they can be modified to direct the complexes to particular types of cells using site-directing molecules. Thus, antibodies or ligands for particular receptors or other cell surface proteins may be employed, with a target cell associated with a particular surface protein.

Any physiologically acceptable medium may be employed for administering the DNA, recombinant viral vectors or lipid carriers, such as deionized water, saline, phosphate-buffered saline, 5% dextrose in water, and the like as described above for the pharmaceutical composition, depending upon the route of administration. Other components can be included in the formulation such as buffers, stabilizers, biocides, etc. These components have found extensive exemplification in the literature and need not be described in particular here. Any diluent or components of diluents that would cause aggregation of the complexes should be avoided, including high salt, chelating agents, and the like.

The amount of therapeutic vector used will be an amount sufficient to provide for a therapeutic level of expression in a target tissue. A therapeutic level of expression is a sufficient amount of expression to decrease blood glucose towards normal levels. In addition, the dose of the nucleic acid vector used must be sufficient to produce a desired level of transgene expression in the affected tissues in vivo. Other DNA sequences, such as adenovirus VA genes can be included in the administration medium and be co-transfected with the gene of interest. The presence of genes coding for the adenovirus VA gene product may significantly enhance the translation of mRNA transcribed from the expression cassette if this is desired.

A number of factors can affect the amount of expression in transfected tissue and thus can be used to modify the level of expression to fit a particular purpose. Where a high level of expression is desired, all factors can be optimized, where less expression is desired, one or more parameters can be altered so that the desired level of expression is attained. For example, if high expression would exceed the therapeutic window, then less than optimum conditions can be used.

The level and tissues of expression of the recombinant gene may be determined at the mRNA level as described above, and/or at the level of polypeptide or protein. Gene product may be quantitated by measuring its biological activity in tissues. For example, protein activity can be measured by immunoassay as described above, by biological assay such as blood glucose, or by identifying the gene product in transfected cells by immunostaining techniques such as probing with an antibody which specifically recognizes the gene product or a reporter gene product present in the expression cassette.

Typically, the therapeutic cassette is not integrated into the patient's genome. If necessary, the treatment can be repeated on an ad hoc basis depending upon the results achieved. If the treatment is repeated, the patient can be monitored to ensure that there is no adverse immune or other response to the treatment.

The invention also provides for methods for expanding a population of pancreatic β-cells in vitro. Upon isolation of the pancreas from a suitable donor, cells are isolated and grown in vitro. The cells which are employed are obtained from tissue samples from mammalian donors including human cadavers, porcine fetuses or another suitable source of pancreatic cells. If human cells are used, when possible the cells are major histocompatability matched with the recipient. Purification of the cells can be accomplished by gradient separation after enzymatic (e.g., collagenase) digestion of the isolated pancreas. The purified cells are grown in media containing sufficient nutrients to allow for survival of the cells as well as a sufficient amount of a β-cell proliferation inducing composition containing a gastrin/CCK receptor ligand and/or EGF receptor ligand, to allow for formation of insulin secreting pancreatic β cells. According to the invention, following stimulation the insulin secreting pancreatic β cells can be directly expanded in culture prior to being transplanted into a patient in need thereof, or can be transplanted directly following treatment with β-cell proliferation inducing composition.

According to the invention, following the stimulation of the growth of newly formed insulin secreting pancreatic β islet cells in culture by incubation of pancreatic islet precursor cells with said islet neogenesis-inducing composition, said cells can then be transplanted into a patient in need thereof, or said precursor cells can be transplated directly following treatment with the islet neogenesis-inducing composition.

Methods of transplantation include transplanting insulin secreting pancreatic β-cells obtained into a patient in need thereof in combination with immunosuppressive agents, such as cyclosporin. The insulin producing cells also can be encapsulated in a semi-permeable membrane prior to transplantation. Such membranes permit insulin secretion from the encapsulated cells while protecting the cells from immune attack. The number of cells to be transplanted is estimated to be between 10,000 and 20,000 insulin producing β cells per kg of the patient. Repeated transplants may be required as necessary to maintain an effective therapeutic number of insulin secreting cells. The transplant recipient can also, according to the invention, be provided with a sufficient amount of a gastrin/CCK receptor ligand and an EGF receptor ligand to induce proliferation, from islet precursor cells, of the transplanted insulin secreting β cells.

The effect of treatment of diabetes can be evaluated as follows. Both the biological efficacy of the treatment modality as well as the clinical efficacy are evaluated, if possible. For example, disease manifests itself by increased blood sugar, the biological efficacy of the treatment therefore can be evaluated, for example, by observation of return of the evaluated blood glucose towards normal. The clinical efficacy, i.e. whether treatment of the underlying effect is effective in changing the course of disease, can be more difficult to measure. While the evaluation of the biological efficacy goes a long way as a surrogate endpoint for the clinical efficacy, it is not definitive. Thus, measuring a clinical endpoint which can give an indication of β-cell regeneration alter, for example, a six-month period of time, can give an indication of the clinical efficacy of the treatment regimen.

The subject compositions can be provided as kits for use in one or more procedures. Kits for genetic therapy usually will include the therapeutic DNA construct either as naked DNA with or without mitochondrial targeting sequence peptides, as a recombinant viral vector or complexed to lipid carriers. Additionally, lipid carriers can be provided in separate containers for complexing with the provided DNA. The kits include a composition comprising an effective agent either as concentrates (including lyophilized compositions), which can be diluted further prior to use or they can be provided at the concentration of use, where the vials may include one or more dosages. Conveniently, in the kits single dosages can be provided in sterile vials so that the physician can employ the vials directly, where the vials will have the desired amount and concentration of agents. When the vials contain the formulation for direct use, usually there will be no need for other reagents for use with the method. Associated with such kits can be a notice in the form prescribed by a governmental agency regulating the manufacture, use or sale of pharmaceuticals or biological products, which notice reflects approval by the agency of manufacture, use or sale for human administration.

The following examples are offered by way of illustration and not by way of limitation.

EXAMPLES

Materials and Methods

The following materials and methods were used in the studies reported by the working examples set forth below except as otherwise noted.

Animals. Mice, FVB and CD strain, were obtained from Taconic Farms, Inc., Germantown, N.Y. The TGF-α transgenic line MT-42 used, which expresses high levels of TGF-α from a metallothionein promoter, is described in Jhappan et al, *Cell*, 61:1137–1146 (1990). Normal Wistar and Zucker rats were allowed normal chow ad libidum with free access to water and were acclimatized for one week prior to initiation of each study. Freshly prepared streptozotocin at a dose of 80 mg/kg body weight was administered by I.V. five to seven days after induction of diabetes, the rats were randomly allocated into groups for subsequent treatment. Hormones, TGF-α and rat gastrin were reconstituted in sterile normal saline containing 0.1% BSA. According to the predetermined treatment schedule for different studies, each animal received a single, daily i.p. injection of either TGF-α or gastrin alone (4.0 μg/kg body weight) or as a 1:1 (w/w) combination (total 8.0 μg/kg) or PBS for a period of 10 days.

INSGAS Transgene Construct. A Pvull-Rsal fragment encompassing nucleotides −370 to +38 of the rat insulin I gene (Cordell, B. G. et al, *Cell*, 18:533–543 (1979)) was ligated into pGem1 (Promega Corp., Madison, Wis.). A 4.4 kb BamH1-EcoR1 fragment containing 1.5 kb introns 1 and 2 and exons 2 and 3 of the human gastrin gene which encodes the preprogastrin peptide precursor was isolated and subcloned downstream of the rat insulin I fragment in pGem1 (Promega). The fragment is described in Wiborg, O., *Proc. Natl. Acad. Sci. USA*, 81:1067–1069 (1984) and Ito, R., et al *Proc. Natl. Acada. Sci.* (USA), 81:4662–4666 (1984). The insulin promoter-preprogastrin INSGAS transgene construct was excised as a 4.8 kb Xba1-EcoR1 fragment.

Generation and Characterization of Transgenic Mice. The fragment, made as described above was prepared for microinjection as follows. It was isolated by agarose gel electrophoresis, purified by CsCl gradient purification, and dialyzed extensively against injection buffer (5 mM NaCl;

01. MM EDTA; 5 mM Tris-HCl pH 7.4). Fertilized oocytes from FVB inbred mice (Taconic Farms, Inc., supra) at the single-cell stage were microinjected using standard techniques. See Hogan, B., et al, *Manipulating the mouse embryo: A laboratory manual*, Cold Spring Harbor, N.Y. (1986). Surviving embryos were then implanted into the oviducts of CD1 (Charles River Laboratories, Inc., Wilmington, Mass.) foster mothers according to procedures in Hogan et al. Transgenic founder mice were identified by DNA blot techniques using DNA isolated from individual mouse tails, and a human gastrin exon 2 probe labelled with 32 dCTP by random priming. F1 mice and their siblings were similarly identified.

Homozygous MT-42 mice containing the MT-TGF-α transgene derived from a CD-1 mouse strain (Jhappan, supra) were crossed with heterozygotic INSGAS mice. After weaning, the offspring were placed on acidified 50 mM $ZnCl_2$ as previously described in order to induce the metallothionein promoter (Jhappan, supra).

Northern Blot Hybridization Assay. For Northern analysis, total RNA was extracted from tissues by the method of Cathala et al, *DNA* 2:329–335 (1983). Samples of 20 μg of total RNA were resolved on a 1% agarose denaturing gel and transferred to nitrocellulose. RNA blots were hybridized with $^{32}$P labelled TGF-α riboprobes or exon 2 of human gastrin that did not cross-hybridize with endogenous mouse gastrin mRNA.

Peptide radioimmunassay of Gastrin. Tissues were extracted and assayed for gastrin immunoreactivity by radioimmunoassay as described previously using antibody 2604 which is specific for biologically active C terminally amidated gastrin in a gastrin radioimmunoassay as described in Rehfeld, J. F., *Scand. J. Clin. Lab. Invest.* 30:361–368 (1972). Tyrosine monoiodinated human gastrin 17 tracer was used in all assays and synthetic human gastrin 17 was used as a standard.

Peptide Radioimmunoassay of TGF-α: Tissues were frozen in liquid nitrogen, ground to a powder with mortar and pestle, and subjected to acid-ethanol extraction as described in Todaro, G. J. et al, *Proc. Natl. Acad. Sci.* (USA), 77:5258–5262 (1980). Extracts were reconstituted with water, and protein concentrations determined with a Coomassie blue dye binding assay (Bio-Rad Laboratories, Hercules, Calif.). Aliquots from the pancreata were tested in duplicate in a TGF-α radioimmunoassay, which measured competition with $^{125}$I TGF-α for binding to a solid-phase rabbit antibody raised against the C-terminus of rat TGF-α (kit from BioTope, Seattle, Wash.).

Blood Glucose. Blood glucose was determined either after overnight fasting or after IPGTT by glucose oxidase method.

Tissue Insulin Analysis. At the end of each study, the animals were sacrificed and pancreas removed. Small biopsies were taken from separate representative sites throughout the pancreas and immediately snap-frozen in liquid nitrogen for immunohistochemistry, protein, and insulin determinations. Snap-frozen pancreatic samples (n=5) were rapidly thawed, disrupted ultrasonically in deionized water and aliquots taken for protein determination and the homogenate subjected to acid/ethanol extraction prior to insulin determination by RIA.

Histological Analysis. The pancreata were removed, weighed, similarly oriented in cassettes, fixed in Bouin's solution and embedded in paraffin by conventional procedures.

Tissue Preparation and Immunohistochemistry. Freshly excised pancreata were dissected, cleared of fat and lymph nodes, fixed in Bouin's fixative, and then embedded in paraffin for sectioning. Routine sections were stained with hematoxylin and eosin according to standard methods. Pancreatic tissue from adult 17 week old MT-TGF-α (MT-42) transgenic mice were immunostained for insulin to examine the effect of TGF-α over-expression on islet development. Insulin positive cells in TGF-α-induced metaplastic ductules were identified using immunoperoxidase staining guinea pig anti-human insulin sera (Linco, Eureka, Mo.); a pre-immune guinea pig serum was used as a control. Immunohistochemistry was performed on 5μ paraffin sections by the peroxidase/antiperoxidase method of Sternberger using a monoclonal rabbit antigastrin antibody. See, Sternberger, L. A., *Immunocytochemistry*, $2^{nd}$ Ed. (1979) NY: Wiley. 104–170.

Point-Counting Morphometrics. The relative volume of islets, ducts, or interstitial cells was quantitated using the point-counting method described in Weibel, E. R., *Lab Investig.*, 12:131–155 (1963). At a magnification of 400×, starting at a random point at one corner of the section, every other field was scored using a 25 point ocular grid. An unbiased but systematic selection of fields was accomplished using the markings of the stage micrometer. Intercepts over blood vessels, fat, ducts, lymph nodes, or interlobular space were subtracted to give the total pancreatic area. A minimum of 5000 points in 108 fields (systematically chosen using the stage micrometer) were counted in each block, with the relative islet volume being the number of intercepts over islet tissue divided by the number over pancreatic tissue. The absolute islet mass or islets was calculated as the relative islet volume times pancreatic weight. See, Lee, H. C., et al, *Endocrinology*, 124:1571–1575 (1989).

Statistical Analysis. Differences between means were compared for significant differences using the Student's t test for unpaired data.

Example 1

Assay for Insulin Production in TGF Transgenic Pancreas

Figure 1B:
FIG. 1B is an image that shows that most ductular cells stained less intensely for insulin, while occasional ductular cells did stain with the same intensity of insulin staining as the adjacent islets.

Immunoperoxidase staining showed numerous insulin staining cells in the metaplastic ducts from the TGF-α transgenic pancreas (FIG. 1A), whereas insulin staining cells were virtually absent from the non-transgenic ducts (less than 6.1%). When at least 600 ductular cells/animal were scored at a final magnification of 400×, insulin positive cells were seen at a frequency of 6.0+/−0.9% (n=5) in the metaplastic ductules of TGF-α transgenic mice. Occasional ductular cells stained with the same intensity of insulin staining as the adjacent islets, but most had less intense staining (FIG. 1B). The low level of insulin staining of the ductular cells resembles that of protodifferentiated cells reported in the ducts of the developing pancreas. Pictet, R. and W. J. Rutter, *Development of the embryonic endocrine pancreas, in Endocrinology, Handbook of Physiology*, ed. R. O. Greep and E. B. Astwood (1972) American Physiological Society: Washington, D.C. 25–66; and Alpert, S. et al *Cell*, 53:295–308 (1988).

However, despite the increased number of insulin positive cells in the metaplastic ducts, the islet mass of the TGF-α transgenic mice was not increased. The islet mass as quantitated by point counting morphometrics was 2.14 mg+/−0.84 (mean+/− se, n=5) in the TGF-α transgenic pancreas compared to 1.93 mg+/−0.46 (n=6) non transgenic litter mates.

Thus, TGF-α over-expression alone did not effect transition of these protodifferentiated duct cells into fully differentiated islets. This implies that islet differentiation requires other factors absent from the adult pancreas of TGF-α transgenic mice. Since differentiation of protodifferentiated islet precursors occurs during late fetal development, factors regulating this transition would likely be expressed in islets during this period. Among the factors expressed in the developing islets are the gastrointestinal peptides, the gastrins.

Example 2

Pancreatic Gastrin Expression from the INSGAS Transgene

Figure 2A:
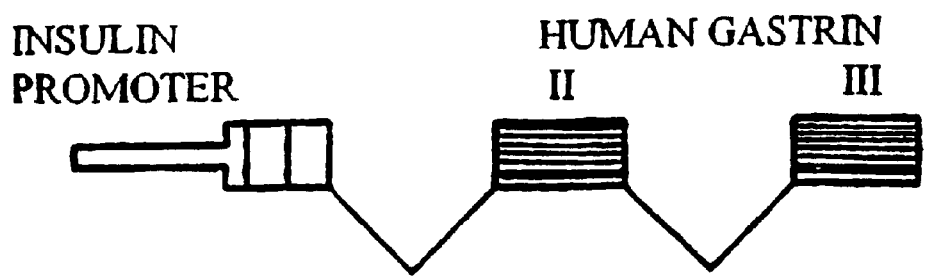
FIG. 2A schematically shows the structure of the chimeric insulin promoter-gastrin (INSGAS) transgene.

To examine the possible role of gastrin in regulating islet differentiation, transgenic mice were created that express a chimeric insulin promoter-gastrin (INSGAS) transgene in which the insulin promoter directs pancreas specific expression of the gastrin transgene (FIG. 2A). Unlike the gastrin gene, insulin gene expression is not switched off after birth. Thus, the INSGAS transgene results in a persistence of gastrin expression in the adult pancreas.

The INSGAS transgene comprised 370 bp of 5' flanking DNA and the first non-coding exon of the rat insulin I gene. Cordell, B., et al, *Cell* 18:533–543 (1979). It was ligated to a BamH1-EcoR1 fragment containing 1.5 kb intron 1 and exons 2 and 3 of the human gastrin gene which encodes the preprogastin peptide precursor. Wiborg, O., et al, *Proc. Natl. Acad. Sci. USA,* 81:1067–1069 (1984); and Ito et al *Proc. Natl. Acad. Sci. USA,* 81:4662–4666 (1984). A 4.8 kb INSGAS fragment was isolated and microinjected into inbred FVB, one cell mouse embryos. Hogan, B. et al, *Manipulating the mouse embroy: A laboratory manual,* (1986) Cold Spring Harbor, N.Y.

Gastrin immunoreactivity in pancreatic and stomach extracts from transgenic and non-transgenic mice was assayed by radioimmunoassay using antisera 2604 (Rehfeld, J., et al, *Scand. J. Clin. Lab. Invest.,* 30:361–368 (1972)) specific for the bioactive amidated C-terminus of gastrin.

Beta cell specific gastrin expression from the INSGAS transgene was observed based on immunostaining of pancreatic tissues with a gastrin monoclonal antibody.

Figure 2B:
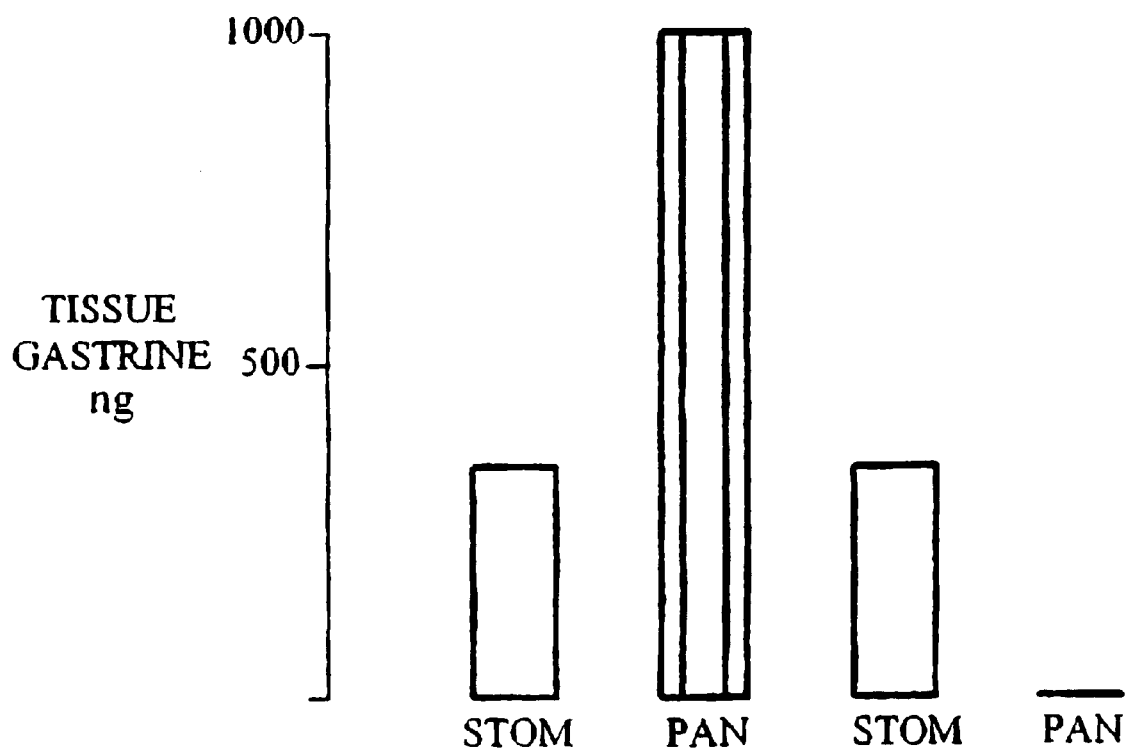
FIG. 2B illustrates that the radioimmunassay of pancreatic extracts from INSGAS transgenic mice shows high levels of gastrin immunoreactivity that exceed the gastrin content in the gastric antrum expressed from the endogenous murine gene. The INSGAS transgenic mice had high expression of gastrin in the postnatal pancreas.

Northern blots of RNA isolated from different tissues of 8 week old INSGAS transgenic mice were hybridized with a human gastrin exon 2 probe. High levels of gastrin transgene mRNA were seen in the pancreas but not in any other tissues. This probe is specific for the human gastrin gene; no hybridization is seen in antral RNA of INSGAS and non-transgenic FVB mice express high levels of murine gastrin mRNA. Radioimmunoassay of pancreatic extracts from INSGAS transgenic mice showed high levels of gastrin immunoreactivity that exceed the gastrin content in the gastric atrium expressed from the endogenous murine gene (FIG. 2B). No gastrin immunoreactivity was detected in pancreatic extracts of non-transgenic control mice (FIG. 2B). The gastrin radioimmunoassay is specific for carboxy amidated precursors, indicating that the gastrin peptide precursor is efficiently processed post-translationally to the bioactive peptide. Immunohistochemistry with a gastrin monoclonal antibody shows pancreatic beta islet cell specific expression of gastrin.

Although the INSGAS transgenic mice had high expression of gastrin in the postnatal pancreas (FIG. 2B), the INSGAS transgenic mice had pancreatic histology identical to controls. Islet mass as quantitated by point-counting morphometrics (Weibel, E. R., *Lab Investig.* 12:131–155 (1963)) was identical in 5–6 week old INSGAS mice (1.78+/−0.21 mg, n=11) and age matched non-transgenic controls (1.74+/−0.18 mg, n=11). Thus, sustained expression of gastrin in the postnatal pancreas alone does not stimulate islet cell growth.

Example 3

Histological Examination of TGF-α and TGF-α/INSGAS Pancreas

Stimulation of islet growth by gastrin may require stimulation by other growth factors to create a responsive population of cells. Therefore, effects of gastrin stimulation were studied in TGF-α transgenic mice which have metaplastic ducts that contain insulin expressing cells resembling protodifferentiated islet-precursors. To assess the interaction between gastrin and TGF-α, three groups of mice were bred with equivalent FVB/CD1 strain genetic backgrounds: non-transgenic control, TGF-α single transgenic and INSGAS/TGF-α double transgenics. All three groups of mice were placed on 50 mM $ZnCl_2$ at 3 weeks of age. At 17 weeks of age, the animals were sacrificed and the pancreas removed for histological evaluation. The pancreas from TGF-α and INSGAS/TGF-α mice had similar gross morphological appearances: resilient, firm and compact in contrast to the soft diffuse control pancreas. TGF-α expression was equivalent in TGF-α and INSGAS/TGF-α groups when measured by Northern blot analysis (data not shown) and by radioimmunoassay. The pancreatic TGF-α immunoreactive peptide levels were 12.2+/−1 and 18.9+/−8 ng/mg protein (Mean +/− SD) in the TGF-α and INSGAS/TGF-α mice, respectively.

Figure 3A:
FIG. 3A is an image of the pancreatic histology of an INSGAS/TGF-α mouse used in the study reported by Example 3. The INSGAS/TGF-α pancreas had some areas of increased ductular complexes and slightly increased interstitial cellularity. The field shown here had the most severely abnormal histology in the five animals used.
Figure 3B:
FIG. 3B is an image of the pancreatic histology of a control mouse from Example 3.

Light micrographs of hematoxylin stained paraffin sections of pancreas from the three groups of mice studied (A: INSGAS/TGF-α; B: FVB/CD1 controls; and C: TGF-α) were made. The INSGAS/TGF-α pancreas had some areas of increased ductular complexes and slightly increased interstitial cellularity; the field shown (FIG. 3A) had the most severely abnormal morphology seen in the five animals; most of the pancreas was indistinguishable from controls (FIG. 3B). In contrast, the field of TGF-α pancreas (FIG. 3C) was typical and showed the interstitial cellularity and fibrosis combined with florid ductular metaplasia described by Jhappan et al, supra.

Pancreatic gastrin synergistically interacts with TGF-α to increase islet mass and inhibit the ductular metaplasia induced by TGF-α over-expression. Mating the homozygous MT-TGF-α (MT-42) mice (TGF-α) with heterozygotic INSGAS mice gave offspring that were either heterozygotic TGF-α single transgenic or double transgenic containing both INSGAS and TGF-α transgenes (INSGAS/TGF-α). Since INSGAS were FVB strain and TGF-α were CD1 strain, TGF-α homozygotes and CD1 controls (CON) were both mated with FVB to produce FVB/CD1 strain background for all three groups of mice. Mice were treated with 50 mM $ZnCl_2$ from 3 weeks until sacrifice at age 17 weeks. The pancreas was removed, weighed, similarly oriented in cassettes, fixed in Bouin's solution and embedded in paraffin. One random section from each animal was used to quantitate the relative volumes of ductules and islets by point-counting morphometrics (Weibel, E. R., *Lab Investig.,* 12:131–155 (1963)). At least 2000 points over tissue were counted as intercepts of a 50 point grid at 170× magnification; the entire section was covered without overlap. The mass of ductules or islets was calculated by multiplying the relative volume and the animal's pancreatic weight. To normalize different mean body weights, the mass was expressed as μg/g body weight. Results are mean and standard errors for 5–6 animals in each group as determined by Student's t test $p<0.05$).

Figure 3C:
FIG. 3C is an image of the pancreatic histology of a TGF-α mouse from Example 3. This field of a TGF-α mouse pancreas from the study reported in Example 3 was typical and showed the interstitial cellularity and fibrosis combined with florid ductular metaplasia that has been described by Jhappan, et al, supra.

Expression of gastrin from the INSGAS transgene reduced the ductular metaplasia caused by TGF-α overexpression. At 17 weeks, the pancreatic histology of the INSGAS/TGF-α mice (FIG. 3A) resembled that of the control pancreas (FIG. 3B) more than that of the TGF-α mice (FIG. 3C).

Figure 4A:
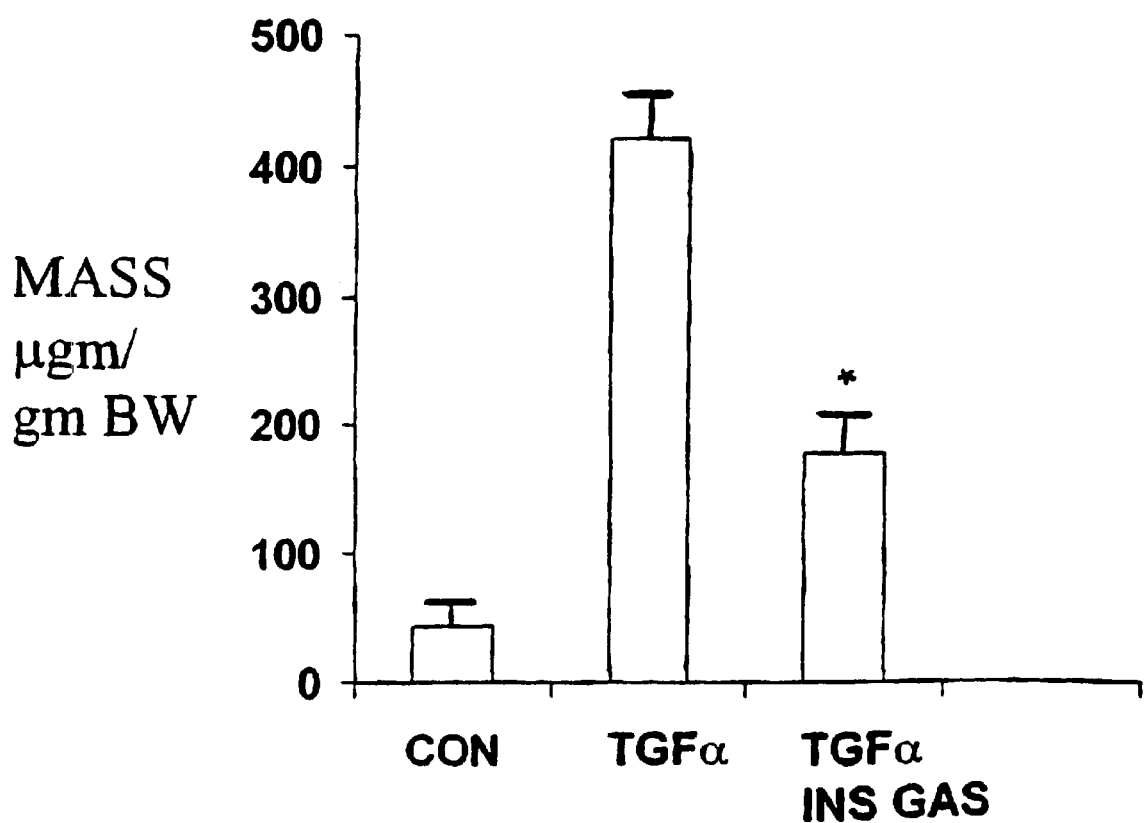
FIG. 4A is a histogram graphically illustrating point= counting morphometric data which confirmed that at 17 weeks the pancreas of the INSGAS/TGF-α mice had lower duct mass than the pancreas of the TGF-α mice based on the study reported in Example 3.
Figure 4B:
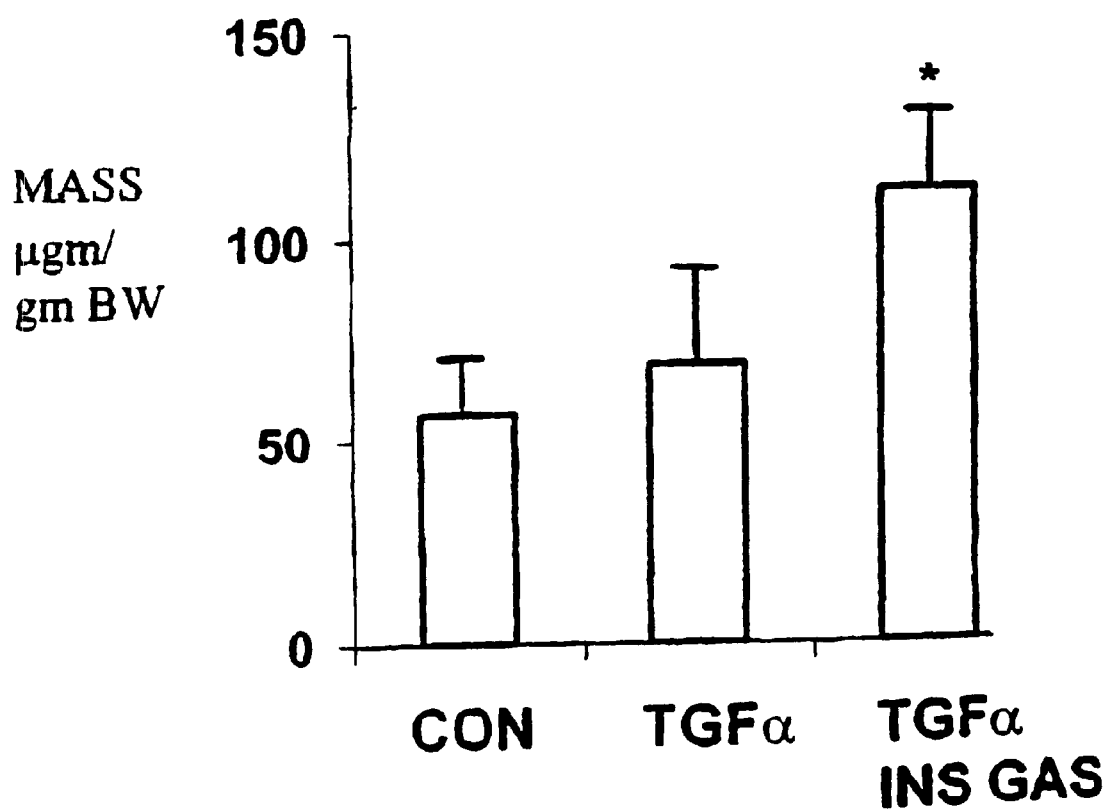
FIG. 4B is a histogram which graphically illustrates point=counting morphometric data which show that co-expression of gastrin and TGF-α in the INSGAS/TGF-α pancreas significantly increased the islet mass compared to the islet mass of the corresponding non-transgenic control mice. Further, TGF-α expression alone does not increase islet mass. These data are based on the studies illustrated in Example 3.
Figure 7A:
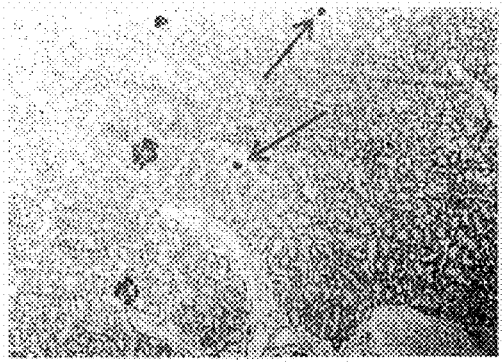
FIGS. 7(A–E) shows the effect of TGF-α and gastrin treatment on β-cell neogenesis in lean and obese Zucker rats. β-cell neogenesis is quantified by differential counting of total β-cells and newly generated single β-cell foci and is expressed as a percentage of total β-cells counted. The percentage of single β-cell foci in lean Zucker rats treated with the growth factor combination was 10.5±0.9 compared to 3.9±1.1 (p=0.004) in the corresponding PBS control (FIGS. 7A and 7B). In the obese Zucker rats, the percent single β-cell foci in the pretreatment group was 8.7±1.3 vs. 4.2±1.1 (p=0.0015) in the corresponding control group (FIGS. 7C and 7D).
FIG. 7E is a 400×magnification of the ductal region of FIG. 7C (indicated by an arrow) and provides clear evidence of the budding of insulin-containing β-cells from the ductal epithelial cells characteristic of β-cell neogenesis.
Figure 7B:
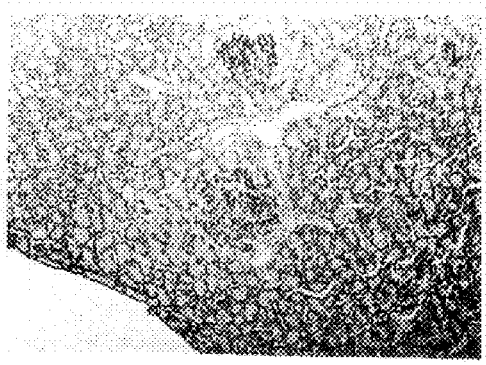
Figure 7C:
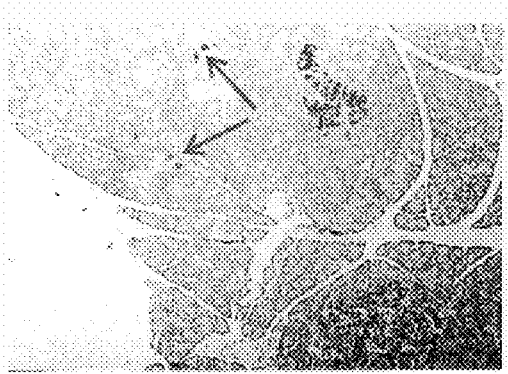
Figure 7D:
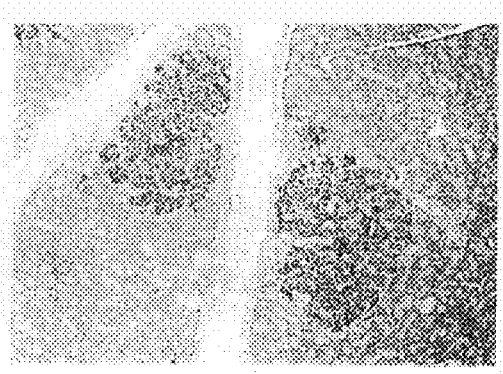
Figure 7E:
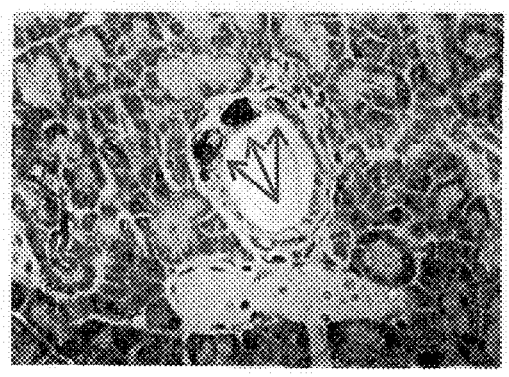

This was confirmed by quantitating pancreatic ductular mass in the TGF-α and INSGAS/TGF-α transgenic mice and the FVB/CD1 controls by point-counting morphometrics (FIG. 4A). Co-expression of gastrin and TGF-α in the INSGAS/TGF-α pancreas also significantly increased the islet mass compared to controls (FIG. 4B), whereas islet mass was not increased by expression of the TGF-α or gastrin transgenes alone. The blood glucose concentration was not significantly different among the three groups of mice.

Example 4

Effects of TGF-α and Gastrin on Pancreatic Insulin Content in Normal Rats

This experiment was designed to study the effects on pancreatic insulin content in non-diabetic animals treated with TGF-α, a gastrin, or a combination of TGF-α and a gastrin as compared to control animals (untreated). Groups (n=5) of normal Wistar rats were assigned to one of the following four treatment groups.

Group I: TGF-α: recombinant Human TGF-α was reconstituted in sterile saline containing 0.1% BSA and was administered i.p. at a dose of 0.8 μg/day for 10 days.

Group II: Gastrin: synthetic Rat Gastrin I was dissolved in very dilute ammonium hydroxide and reconstituted in sterile saline containing 0.1% BSA. It was administered i.p. at a dose of 0.8 μg/day for 10 days.

Group III: TGF-α+Gastrin: a combination of the above preparations was administered i.p. at the dose levels given above for 10 days.

Group IV: Control animals received an i.p. injection of vehicle alone for 10 days.

At the end of the study period (10 days), all animals were sacrificed and samples of pancreas taken as follows: five biopsy specimens (1–2 mg) of pancreatic tissue were taken from separate representative sites in each rat pancreas and immediately snap frozen in liquid nitrogen for analysis of insulin content. For analysis of pancreatic insulin content, the snap frozen pancreatic samples were rapidly thawed, disrupted ultrasonically in distilled water and aliquots taken for protein determination and acid/ethanol extraction prior to insulin radioimmunoassay (Green et al, (1983) *Diabetes* 32:685–690). Pancreatic insulin content values were corrected according to protein content and finally expressed as μg insulin/mg pancreatic protein. All values calculated as mean +/− SEM and statistical significance evaluated using Student's 2-sample t-test.

TABLE 1

Treatment of Normal Rats with TGF-α and Gastrin

| Treatment | Pancreatic Insulin Content (μg insulin/mg protein) |
|---|---|
| Control | 20.6 +/− 6.0 |
| TGF-α | 30.4 +/− 7.4* |
| Gastrin | 51.4 +/− 14.0** |
| TGF-α + Gastrin | 60.6 +/− 8.7*** |

TABLE 1-continued

Treatment of Normal Rats with TGF-α and Gastrin

| Treatment | Pancreatic Insulin Content (μg insulin/mg protein) |
|---|---|

*TGF-α vs. control, p = 0.34;
**gastrin vs. control, p = 0.11;
***combination of TGF-α and gastrin, p = 0.007.

As shown in Table 1, above, pancreatic insulin content was significantly increased (p=0.007) in the TGF-α+gastrin treated animals as compared to control animals; there was an approximately three-fold increase in pancreatic insulin content as compared to control animals. These data support the hypothesis that the combination of TFG-α and gastrin does produce an increase in the functional islet β-cell volume. This increase reflects an overall condition of β-cell hyperplasia (increase in number) rather than β-cell hypertrophy (increase in size of individual β-cells).

Example 5

Effect of Combination of TGF-α and Gastrin on Pancreatic Insulin Content in Diabetic Animals The second experiment was designed to determine whether the combination of TGF-α and gastrin could increase pancreatic insulin content in diabetic animals (streptozotocin (STZ) treated) to levels comparable to those in normal (non-STZ treated) animals.

Normal Wistar rats received a single iv injection of STZ at a dose of 80 mg/Kg body weight. This dose of STZ was intended to ensure that the study animals were rendered diabetic but that they retained a functioning but reduced β-cell mass. The STZ was dissolved immediately before administration in ice-cold 10 mM citric acid buffer. The animals were monitored daily; persistent diabetes was indicated by glycosuria and confirmed by non-fasting blood glucose determinations. One week after induction of diabetes, rats were randomly allocated into two groups (n=6) as follows.

Group I: TGF-α +Gastrin: STZ diabetic rats were treated with a single i.p. injection of a combination of recombinant human TGF-α and synthetic rat Gastrin 1; both preparations were administered at a dose of 0.8 μg/day for 10 days.

Group II: Control: STZ diabetic rats received an i.p. injection of vehicle alone for 10 days.

At the end of the study period, all animals were sacrificed and samples of pancreas taken and analyzed as described in Example 4 and the results are given in Table 2.

TABLE 2

Treatment of Streptozotocin Rats with TGF-α and Gastrin

| Treatment | Pancreatic Insulin Content (μg Insulin/mg protein) |
|---|---|
| Control (STZ alone) | 6.06 +/− 2.1 |
| STZ plus TGF-α + Gastrin | 26.7 +/− 8.9 |

The induction of diabetes by STZ was successful and produced a moderate but sustained degree of hyperglycemia. Total insulinopaenia was not sought so as to ensure that the study animals retained a functioning, but reduced β-cell mass.

As shown in Table 2, above, the pancreatic insulin content of the control streptozotocin treated animals was less than one third that of normal rats (20.6±6.0 mg insulin/mg protein, see Table 1 above) as a result of destruction of β-cells by the STZ. In STZ animals treated with a combination of TGF-α and gastrin, the pancreatic insulin content was more than four-fold that of the animals which received STZ alone, and statistically the same as that of normal rats.

Diabetes mellitus is a disease in which the underlying physiological defect is a deficiency of β-cells as a result either of destruction of the β-cells due to auto-immune processes or of exhaustion of the potential for the β-cells to divide due to chronic stimulation from high circulating levels of glucose. The latter eventually leads to a situation when the process of β-cell renewal and/or replacement is compromised to the extent that there is an overall loss of β-cells and a concomitant decrease in the insulin content of the pancreas. The above results demonstrate that a combination of TGF-α and gastrin can be used to treat diabetes by stimulating the production of mature β-cells to restore the insulin content of the pancreas to non-diabetic levels.

Example 6

Effects of TGF-α and Gastrin on IPGTT in STZ-Induced Diabetic Animals

Two groups (average body weight 103 g) of STZ induced diabetic Wistar rats (n=6/group) were treated for 10 days with a daily i.p. injection of either a combination of TGF-α and gastrin or PBS. Fasting blood glucose was determined for all rats on days 0, 6, and 10. In order to establish that this insulin was secreted and functional, IPGTT tests were performed. At day 10, intraperitoneal glucose tolerance tests (IPGTT) were performed following an overnight fast. Blood samples were obtained from the tail vein, before and 30, 60 and 120 minutes after administration of an i.p. glucose injection at a dose of 2 g/kg body weight. Blood glucose determinations were performed as above. The blood glucose levels were similar in both study groups at time 0 but the TFGα and gastrin treated rats demonstrated a 50% reduction in blood glucose values (see FIG. 5), as compared to control rats at 30, 60, and 120 min. following the i.p. glucose load.

Example 7

Effects of TGF-α and Gastrin on Body Weight Gain and Insulin Content in Diabetes Prone Animals Zucker rats were obtained at 30 days of age approximately 10–15 days prior to development of obesity. Besides the diabetes prone Zucker rats (genotype fa/fa, autosomal recessive mutation for obesity and diabetes), lean non-diabetic littermates (genotype +/+) also were included in the study as described below. The rats were monitored daily for development of obesity and diabetes by determining body weight and blood glucose. The onset of diabetes in Zucker rats usually started between days 45–50 and was confirmed by a significant increase in blood glucose levels, as compared to the levels in age-matched lean controls.

The study included 5 groups of 5 rats each as described in Table 3. Groups 1 and 2 (lean, non-diabetic) were treated with a TGF-α and gastrin combination or PBS respectively from day 0 to day 10. Groups 3, 4 and 5 included obese, early diabetic Zucker rats, genotype fa/fa. Group 3 received a combination pretreatment for 15 days (day −15 to day 0) prior to onset of diabetes and continuing post onset of diabetes for 10 additional days (day 0 to day 10). Group 4 was treated with a combination of TGF-α and gastrin for 10 days after onset of diabetes and Group 5 was treated with PBS over the same time period. At the end of the study, the rats were sacrificed and the pancreas removed. Small biopsies were taken from separate representative sites for protein and insulin determinations as described above.

The body weight gain in obese diabetic Zucker rats with pretreatment, treatment only or with saline (groups 3, 4, and 5 in Table 3) did not show any significant differences among the groups. It is interesting to note that even prolonged treatment (25 days, group 3) with TGF-α+gastrin was without effect on normal weight gain. Within error limits body weight gain was identical in all the groups.

The effect of TGF-α+gastrin treatment on fasting blood glucose in the obese Zucker rats was compared to the corresponding PBS controls. Fasting blood glucose was first significantly increased by day 15 (4.0±0.6 vs. 5.0±0.2) and this time point was chosen as the starting time for the 10-day treatment period with TGF-α+gastrin or with PBS control. Fasting blood glucose levels were not significantly altered by the TGF-α+gastrin treatment or by PBS. Fasting blood glucose values were lower in lean, as compared to obese animals whether or not they were treated with the growth factors or with PBS.

TABLE 3

| Group | Geotype | Condition | Pretreatment ± Treatment (days) | PBS Control | Body Wt Gain (% ± SE) |
|---|---|---|---|---|---|
| 1. | +/+ | lean, non-diabetic | None | Yes | 117 ± 2.1 |
| 2. | +/+ | lean, non-diabetic | 0 + 10 | No | 119 ± 1.9 |
| 3. | fa/fa | obese, early diabetic | −15 + 10 | No | 202 ± 15 |
| 4. | fa/fa | obese, early diabetic | 0 + 10 | No | 119 ± 1.0 |
| 5. | fa/fa | obese, early diabetic | None | Yes | 129 ± 1.3 |

The results of treatment with TGF-α and gastrin in the Zucker rat model of Type 2 diabetes showed no significant differences in blood glucose levels between the treatment and control groups, probably reflecting the transient hypoglycemic effect following a prolonged period (18 hrs) of fasting. The immunohistochemical studies revealed significant increases in the number of single foci of insulin containing cells in the TGF-α and gastrin treated animals, as compared to control animals. These findings demonstrated an increase in single β-cells in adult rat pancreas following treatment with TGF-α and gastrin. Interestingly, such single β-cell foci are not commonly seen in adult (unstimulated) rat pancreas. These findings support a therapeutic role for TGF-α and gastrin in Type 1 and Type 2 diabetes since treatment is targeted at both β-cell neogenesis and replication.

The present invention is based in part on studies which demonstrated numerous insulin staining cells in the TGF-α-induced metaplastic ductules. The low level of exocrine and endocrine gene expression in the metaplastic ductal cells resembled that of protodifferentiated ductal cells seen in the early stage of fetal pancreatic development. Formation of islets (neogenesis) results from proliferation and differentiation of these protodifferentiated insulin expressing cells. Histologically this is manifested as islets appearing to bud from the pancreatic ducts (nesidioblastosis). In the MT-42 TGF-α transgenic mice, ductular metaplasia was not seen in the immediate post-natal period, but only at 4 weeks of age.

This indicates that TGF-α over-expression induced insulin expression in duct epithelia rather than prolonging the persistence of islet precursors found in fetal pancreatic ducts. Although the metaplastic ductules contained numerous insulin positive cells, the islet mass of the TGF-α transgenic mice was not increased over controls. The studies reported above demonstrate that complete islet cell neogenesis is reactivated in vivo in mammals in the ductular epithelium of the adult pancreas by stimulation with a gastrin/CCK receptor ligand, such as gastrin, and/or an EGF receptor ligand, such as TGF-α. Studies are reported on the transgenic over-expression of TGF-α and gastrin in the pancreas which elucidate the role of pancreatic gastrin expression in islet development and indicate that TGF-α and gastrin each play a role in regulating islet development. Thus, regenerative differentiation of residual pluripotent pancreatic ductal cells into mature insulin-secreting cells is a viable method for the treatment of diabetes mellitus, by therapeutic administration of this combination of factors or compositions which provide for their in situ expression within the pancreas or by in vitro incubation of pancreatic tissue with this combination of factors.

The present invention is not limited by the specific embodiments described herein. Modifications that become apparent from the foregoing description and accompanying figures fall within the scope of the claims.

Various publications are cited herein, the disclosures of which are incorporated by reference in their entirety.

What is claimed is:

1. A method for expanding a population of pancreatic beta cells, said method comprising:

providing said pancreatic beta cells with a sufficient amount of a gastrin/CCK receptor ligand and an epidermal growth factor receptor ligand to induce proliferation of said pancreatic beta cells, whereby an expanded population of pancreatic beta cells is obtained.

2. A composition comprising:

a cell culture comprising a plurality of pancreatic β cells and a growth medium consisting essentially of a sufficient amount of a gastrin receptor ligand and an epidermal growth factor receptor ligand to induce proliferation of said pancreatic β cells.

3. A composition comprising:

a cell culture comprising a plurality of proliferating pancreatic β cells.

* * * * *